United States Patent [19]

Hille et al.

[11] Patent Number: 5,681,413
[45] Date of Patent: Oct. 28, 1997

[54] PRODUCTION OF TRANSDERMAL THERAPEUTIC SYSTEMS

[75] Inventors: Thomas Hille, Neuwied; Lothar Deurer, Koblenz; Peter Steinborn, Neuwied; Ludwig Grader, Andernach; Dieter Anhäuser, Melsbach, all of Germany

[73] Assignee: LTS Lohmann Therapie-Systeme GmbH & Co., Neuwied, Germany

[21] Appl. No.: 403,754
[22] PCT Filed: Sep. 15, 1993
[86] PCT No.: PCT/EP93/02495
§ 371 Date: May 9, 1995
§ 102(e) Date: May 9, 1995
[87] PCT Pub. No.: WO94/07449
PCT Pub. Date: Apr. 14, 1994

[30] Foreign Application Priority Data

Sep. 25, 1992 [DD] German Dem. Rep. ......... 42 32 279.0

[51] Int. Cl.⁶ .................. A61F 13/02; B65C 1/02
[52] U.S. Cl. .................. 156/238; 156/247; 156/249; 156/256; 156/300; 156/520
[58] Field of Search .................. 156/238, 247, 156/248, 249, 256, 300, 301, 302, 519, 520, 541

[56] References Cited

U.S. PATENT DOCUMENTS

| | | | |
|---|---|---|---|
| 1,977,046 | 10/1934 | Cumfer | 156/520 |
| 2,372,617 | 3/1945 | Trew | 156/520 |
| 3,707,422 | 12/1972 | Helm | 156/520 |
| 4,664,736 | 5/1987 | Faasse, Jr. | 156/300 |
| 4,715,926 | 12/1987 | Murasaki | 156/520 |
| 4,838,982 | 6/1989 | Klaeser et al. | 156/520 |
| 4,991,378 | 2/1991 | Dotta | 156/252 |
| 5,268,179 | 12/1993 | Rudella | 156/73.1 |
| 5,405,486 | 4/1995 | Sablotsky et al. | 156/250 |

Primary Examiner—Jill L. Heitbrink
Attorney, Agent, or Firm—Wenderoth, Lind & Ponack

[57] ABSTRACT

The invention provides a process for the production of transdermal therapeutic systems. A layer containing active substance is initially present as a tape or web in the form of a laminate, with a carrier layer and, possibly, further auxiliary layers and/or protective layers or the like. The active substance is then transferred from this layer, either by itself or in combination with at least one further layer, in sections, to the center of a second, wider web. The process is characterized by the fact that the tape or web (1) and the second web (2) are moved forward by steps, with different phases of motion and inoperative phases and/or different step lengths and/or differing speeds and that in the same appliance, during each inoperative or stationary phase of the webs (1, 2) the subdivision of the layer containing active substance and, as the case may be, of one or more further layers, with the exception of the carrier layer, takes place in phases and in the same forward direction, at right angles to the direction of web, into sections (7, 8) containing active substance of a size suitable for the user, and their transfer to the second web, the carrier sheet (9) being removed, in preferably equal intervals, using a transfer device which can be moved backwards and forwards in the direction of the web.

9 Claims, 4 Drawing Sheets

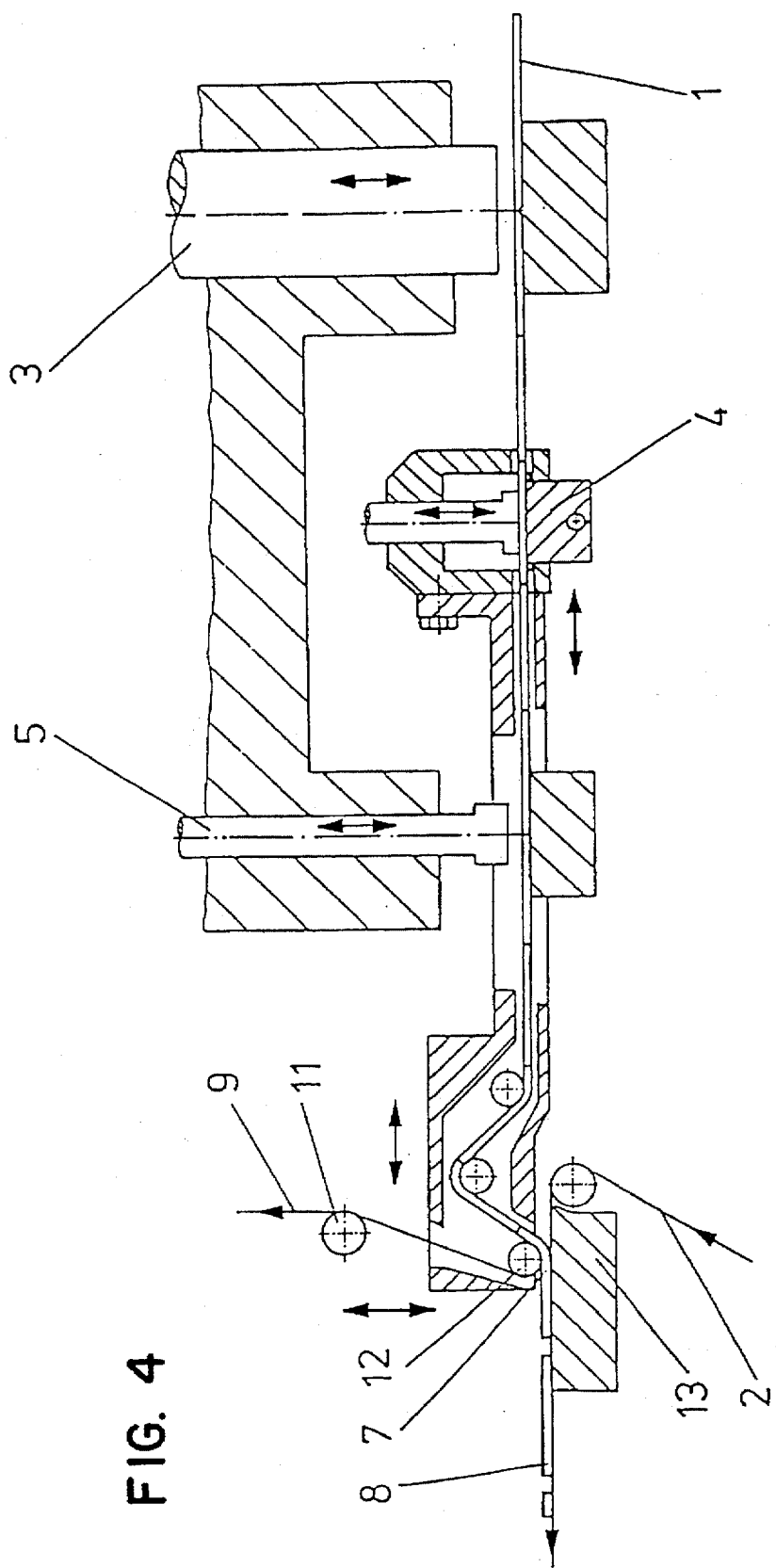

PRODUCTION OF TRANSDERMAL THERAPEUTIC SYSTEMS

BACKGROUND OF THE INVENTION

A process for the continuous production and filling of plaster packaging with an active substance to be administered transdermally is known from DE-PS 32 04 582. In this process the active substance is applied to a carrier sheet, one portion at a time, at fixed intervals, is covered up by sections of metallic cover foil and then covered by an elastic skin adhesive sheet, using an interleaf sheet surrounding said sections of metallic cover foil, the skin adhesive sheet being adhesive on one side, namely that side opposite the interleaf sheet. After this, the portions of active substance are punched out, in the desired size, together with the surrounding sheet layers. This process involves relatively large technical resources and produces comparatively large amounts of surplus material.

A process for the continuous production of transdermal therapeutic plasters has also been suggested in which, to begin with, a laminate is produced by coating an intermediate carrier sheet with a preparation capable of flowing and containing active substance. This laminate is then trimmed to size, into strips of a given width, and, in further process steps, into sections of a determined length, containing active substance, the latter being applied, finally, at predetermined intervals, to a protective sheet covering them all over and, finally, being divided into individual plasters by separating the protective sheet transverse to the path of the belt, between the sections containing active substance. The process, it is true, solves very favourably the set task of obviating or minimizing the loss of active substance, as far as possible, but it is, however, comparatively complicated, owing to its many process steps.

DESCRIPTION OF THE INVENTION

It is the object of the invention under consideration, therefore, to transfer individual sections containing active substance, at high speed, very accurately, and without loss of the active substance, one after the other, at exactly predetermined intervals, from a first web to a second web overlapping the sections all round, in a technically simple and reliable manner. This task is solved, according to the invention, by a process in which a tape or web (1) and a second web (2) are moved forward by steps, with different phases of motion and stationary or inoperative phases and/or different step lengths and/or differing speeds and that, in the same appliance, in phase, in the same forward direction, during each inoperative or stationary phase of the webs (1,2), the subdivision of the layer containing active substance and, possibly, of one or more further layers, with the exception of the carrier layer, takes place at right angles to the direction of the web, into sections (7,8) containing active substance of a size suitable for the user, and their transfer to the second web, the carrier sheet (9) being removed, in preferably equal intervals, using a transfer device moving backwards and forwards in the direction of the web. Practical, additional embodiments of the invention are additionally described herein.

By applying the sections containing active substance from the first web to the second web during a stationary or inoperative phase of the webs, it is no longer necessary to exactly synchronize the speed of the webs in their phase of movement, and it will be possible to adjust the required forward feed lengths of the web exactly, in a simple manner, the distances between the sections containing active substance being easily varied in the required manner, by increasing the length of the forward feed length of the second web correspondingly by having different movement or stationary phases and/or lengths of cut and/or speeds of the two webs.

The advantage is the employment of a transfer device with a so-called dispenser edge, known, as such, from the application of labels to objects in labelling equipment, as they are known, for example, from DE-OS 15 11 873, DE-PS 25 55 910, DE-OS 32 33 546, DE-PS 36 18 542 and DE-GM 83 21 825. High production speeds can be realized thereby, in particular, through the use of a discharge or transfer device with movement of its own. The sections containing active substance are detached, to begin with, from the carrier sheet of the first web, at the dispenser edge and laid onto the second web immediately thereafter. The transfer can also be carried out in the reverse order, with the use of a laminating roll, i.e. the first web is laminated in its original compound onto the second web, first of all, the carrier sheet of the first web being removed again immediately thereafter. If this lamination takes place in sections in the stationary phase of the webs, through the self-movement of the laminating roll, it is possible to realize high production speeds. The formation of adhesive bridges is prevented reliably, in a favourable manner, owing to the fact that both the severance of the layer containing active substance and the transfer of the sections containing active substance formed thereby at predetermined intervals, immediately after one another, are undertaken "on line", on one and the same device.

The realization of the process can be effected in such a way that the layer containing active substance is placed in the first web-shaped laminate, between an auxiliary layer and a sheet furnished with an adhesive-repellent, for instance siliconized, sheet. The sections containing active substance then consist of the self-adhesive layer containing active substance and the auxiliary layer and are transferred by means of the discharge or transfer device to the second web, equipped to be adhesive-repellent, in such a way that the layer containing active substance lies directly upon the sheet which is adhesive-repellent. The movable dispenser edge is employed, in a favourable manner, as a transfer device.

Another possibility as regards the organization of the process is, for example, the provision of a second web with a self-adhesive coating. The sections containing active substance, which, in turn, are composed of the layer containing active substance and an auxiliary layer, are transferred to the second web in such a way that the auxiliary layer lies directly on the self-adhesive second web. Both the movable dispenser edge and the movable laminating roll can be used as transfer devices. Further possibilities of realizing the process consist of providing the layer containing active substance in the first web-shaped laminate as a self-adhesive layer on a carrier sheet which is adhesive-repellent. The sections containing active substance then consist only of the self-adhesive layer and are transferred to the second web by means of the discharge or transfer device. The layer containing active substance in the first, web-shaped laminate can also be arranged, instead, as a non-self-adhesive layer on a carrier sheet. The sections containing active substance then consist only of the non-self-adhesive layer and are transferred by means of the discharge or transfer device to a second, self-adhesive coated web. Provision can also be made for the layer containing active substance in the first web to be arranged as a laminate consisting of three or more layers, on a carrier sheet. The sections containing active substance are then transferred by means of the discharge or transfer device in one order or the other of the successive layers to the second web.

If a clamp device is employed for the step-by-step transport of the first web in the process according to the invention, then this will determine the length of the sections containing active substance. The movement of the discharge or transfer device can be synchronized with the movement of the clamp device. This can be achieved in a simple and reliable manner, for example through a direct, mechanical connection. Complicated control measures are then not required and the full length of each section containing active substance is handed over exactly. The scale of movement of the transfer device is determined, as a result, by the size of the sections to be transferred. Other mechanisms, e.g. a roller device or the like can, of course, be used instead of a clamp device.

If the transfer device can perform a movement vertical to the direction of the web in addition to its movement in the direction of the web, then the advantage is that the sections containing active substance can be pressed against the second web during or after their transfer to the latter, particularly if the sections containing active substance are arranged on the underside of the carrier sheet of the first web.

The removal of the delaminated first carrier sheet on the movable transfer device can happen in such a favourable manner that the sheet is pulled off during the back and forward motion of the transfer device. For that purpose a first deflection roll, attached directly to the transfer device, and, in addition, a second fixed deflection roll are provided. The rolls are arranged in such a way, thereby, that the carrier sheet on the transfer device is deflected by an angle of about 135 to 180 degrees, and by the first deflection roll in the opposite direction, on average by about 120 degrees. The angle in the front position of the transfer device ought, therefore, not to amount to less than 100 degrees and in the rear position to not more than 140 degrees. This arrangement of the deflection rolls for the removal of the first carrier sheet on the transfer device means that a smooth and stress-free running of the machine can be achieved.

The process according to the invention can also be implemented in such a way that the layer containing active substance is transferred to a non-adhesive or self-adhesive web on its own or together with one or more auxiliary layers. An important advantage ensues, as a result, if the transfer device is coupled mechanically directly with the clamp device of the first web. The length of stroke of the transfer device then always corresponds to the length of the sections to be transferred and all control problems are eliminated.

BRIEF DESCRIPTION OF THE DRAWINGS

The invention is shown in the drawing in examples of Embodiments and will be elucidated using these in the following.

FIGS. 1 to 3 show various phases of an embodiment of the process according to the invention and FIG. 4 shows another embodiment.

In FIG. 1, 1 stands for the first web-shaped laminate or the first web, whereby this can, seen from the bottom towards the top, consist, in a way which is not shown, for example of a 50 µm thick PET film, siliconized on both sides, which acts as a carrier sheet; a layer containing active substance with a weight per area of 100 g/m², which comprises 57% of a solvent polyacrylate as a pressure-sensitive adhesive, 25% of a softener, 10% of a polymethacrylate and 8% of the active substance physostigmine base; and of a 25 µm thick PET auxiliary sheet; and can be 35 mm wide. The second web 2 is 56 mm wide and is formed, for example, to begin with solely by using a 100 µm strong PET film siliconized on both sides. Other arrangements or sequences of layers are, of course, possible, in a great variety of variants.

Figure 1:
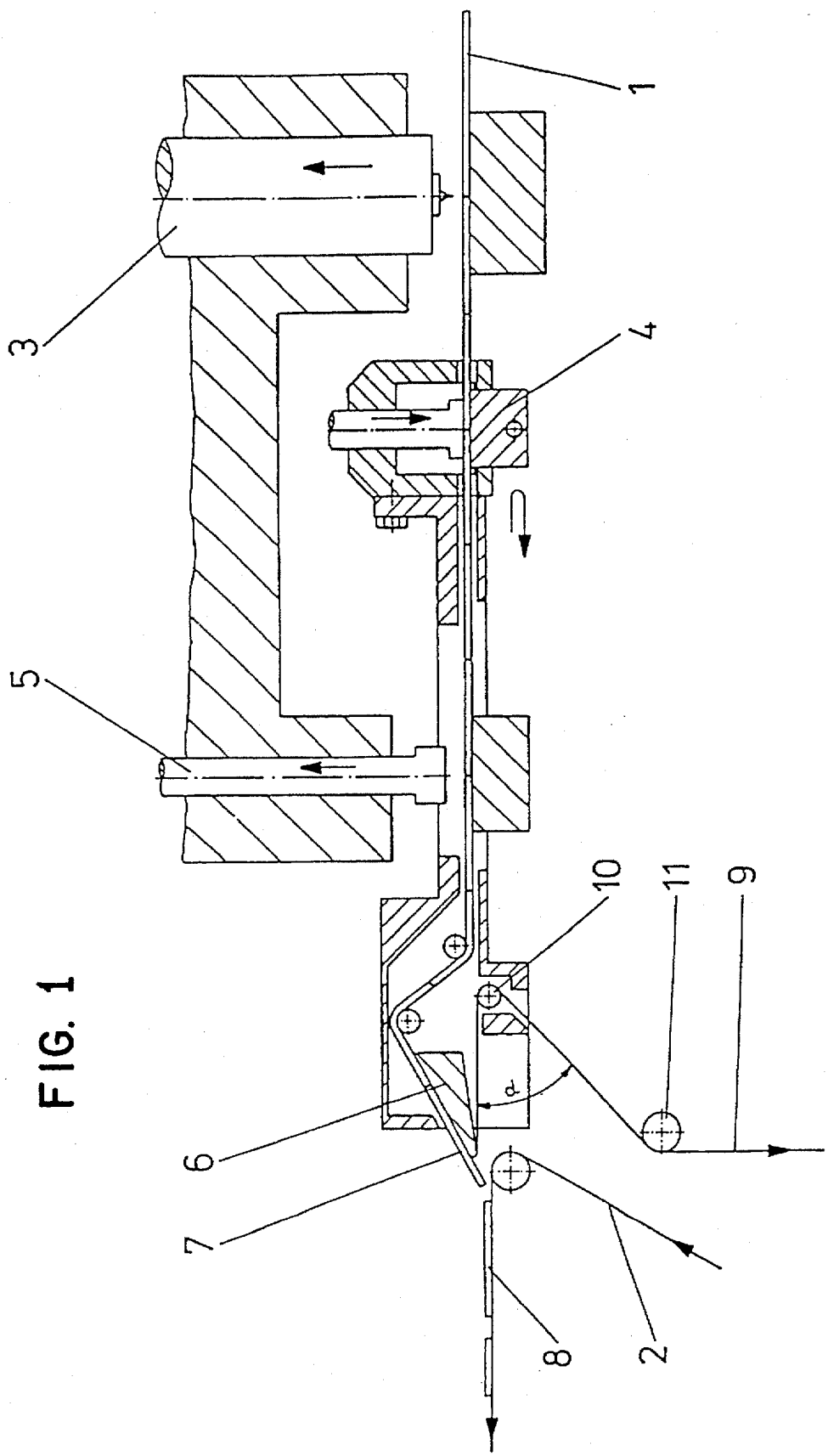

The auxiliary sheet and the layer containing active substance are cut by means of a straight cut running vertically to the direction of the web, using the punch or cutting device 3, square sections measuring 35 mm×35 mm being the result. The carrier sheet is not cut in so doing, in other words it remains intact. With the aid of the movable clamp 4 of the clamp device or, in its stead, also a roller device or the like, the first web 1 can be transported from right to left in the movement phase and held tight with the aid of the holding-down device 5 in the stationary phase which follows. Sections 7 containing active substance are separated from the carrier sheet 9 at the dispenser edge 6 of the transfer device. The movability of the webs and of the parts of the device is indicated respectively by means of arrows or double arrows.

FIG. 1 shows the dispenser edge in its rear dead centre. Section 8 has detached itself from the dispenser edge and has been applied to the second web 2 completely. Webs 1 and 2 are still in the stationary phase but the holding-down clamp 5 has already opened and clamp device 4 has closed.

Figure 2:
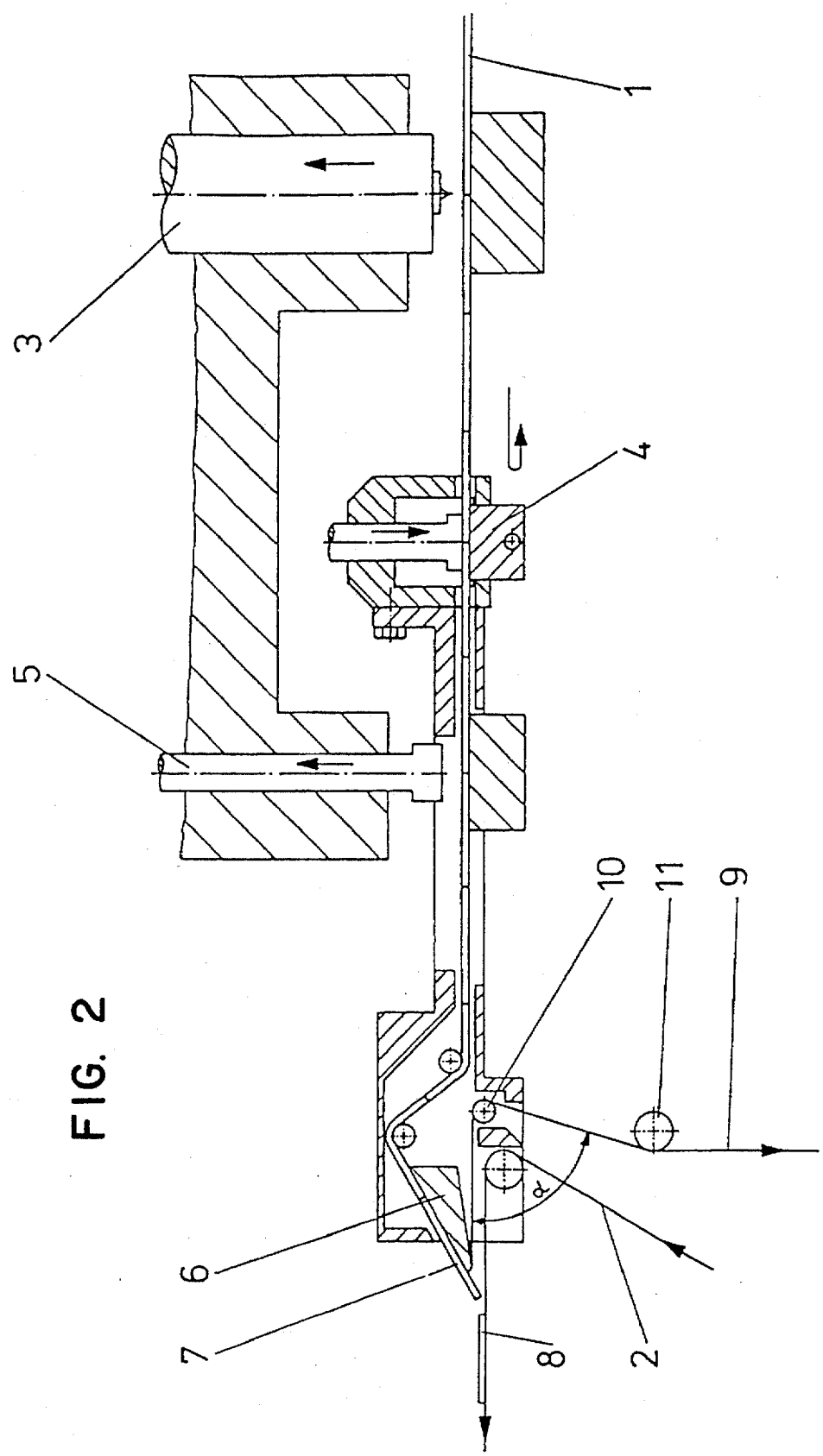

In FIG. 2 the front dead centre has been reached. The clamp device 4, dispenser edge 6 and web i have been moved forward by 35 mm. At the same time web 2 has been moved forward by 56 mm, resulting in the formation of a space of 21 mm between the sections 7 and 8 containing active substance, as described.

Figure 3:
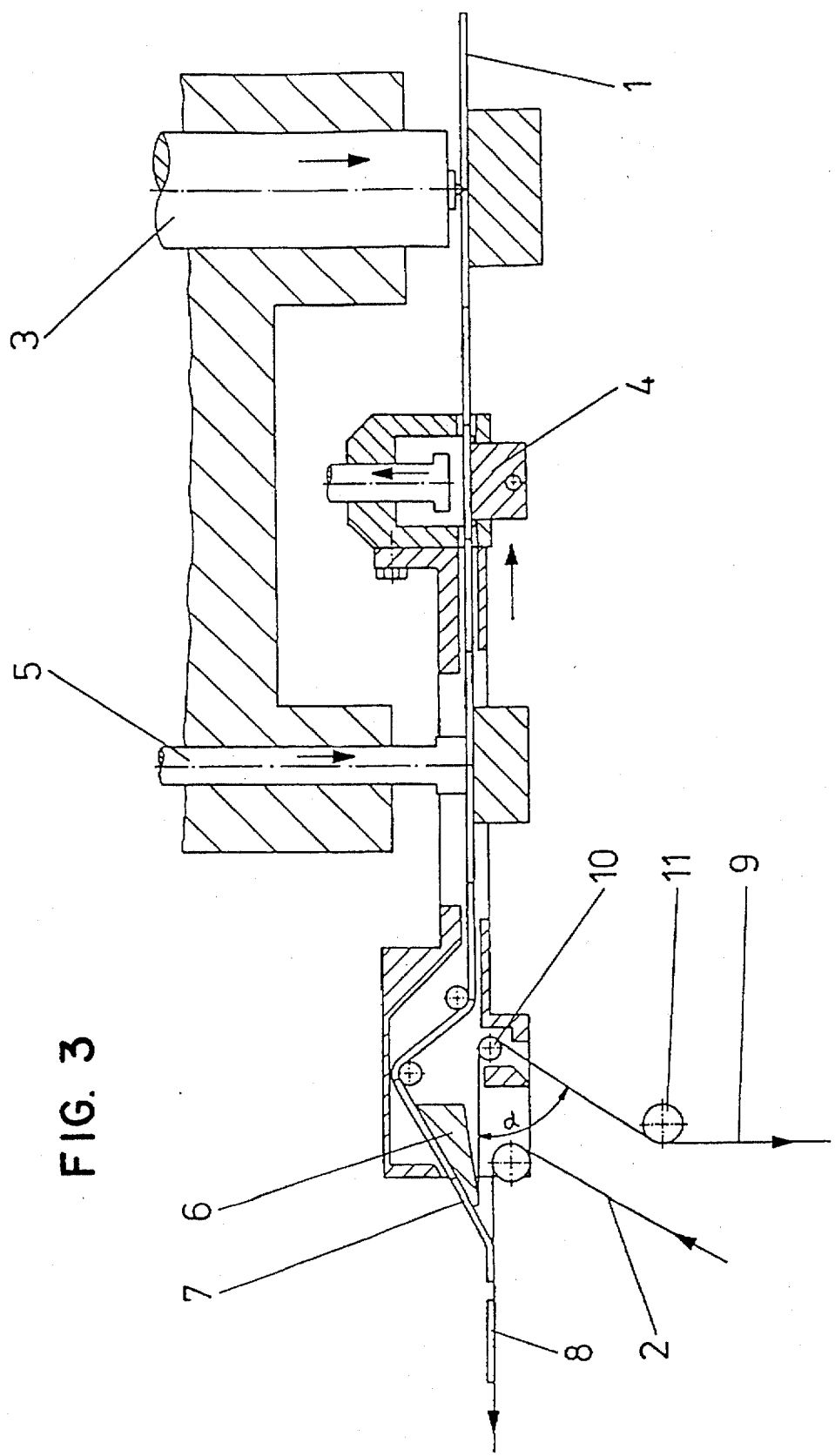

In FIG. 3, finally, webs 1 and 2 are at rest and punch 3 is just performing the cutting act. The opened clamp device 4 and the dispenser edge 6 are moving backwards together, during which section 7 containing active substance is applied to the second web. The carrier sheet 9 is removed at the same time. As can be seen from FIGS. 1 to 3, the division of the layer containing active substance and the transfer of the sections containing active substance take place essentially immediately after one another. The dispenser edge 6 is connected mechanically to the clamp special feature 4, so that they perform the same movement. Carrier sheet 9 runs over both the deflection roll 10 moved together with dispenser edge 6 as well as over the fixed deflection roll 11. The carrier sheet is deflected here by about 155 degrees by dispenser edge 6 and by an angle of about 180 degrees-α, which lies between about 120 degrees in the front position (FIG. 2) and about 135 degrees in the rear position of the dispenser edge (FIG. 1) by the movable deflection roll 10.

In the embodiment according to the invention in accordance with FIG. 4, the sections containing active substance are first applied to the second web and then separated from the carrier sheet. The first web-shaped laminate 1 exhibits a layer containing active substance lying underneath and a carrier sheet lying on top. The second web 2 consists of a self-adhesive coated sheet. The layer containing active substance lying underneath is divided by means of punch 3, using a straight cut running vertically to the direction of the web. The laminating roll 12, which is moved backwards and forwards in synchronism with the clamp device 4, indicated by the double arrow, serves as a transfer device. In addition, indicated also by means of the double arrow, it performs a movement vertical to the web, so that it runs freely during the forward stroke and presses the two webs onto the laminating table 13 during the reverse stroke. In this way section 7 containing active substance is laminated to the self-adhesive web 2 and immediately after that the carrier sheet 9 is pulled off via the fixed roll 11.

During the production of the plaster according to the invention, a larger or smaller number of layers or auxiliary layers and/or protective layers can be provided, as the occasion demands, i.e. depending upon what the plaster is to be used for; it goes without saying that materials suitable for the case in question, such as metals—by preference aluminium—polymers or even textiles—come into question for the individual layers. The individual layers formed thereby are, depending on their respective application or the task to be accomplished, self-adhesive or even adhesive-repellent layers permeable to active substance or also impermeable to active substances, flexible or inflexible ones.

It is important, in any case, that sections 7, 8 of web 1 containing active substance, which can, of course, exhibit any desired form, such as rectangular, square, oval, circular or the like, but which, considering the need to prevent the loss of active substance, ought preferably to be rectangular or square, are conveyed further by the non-interrupted carrier sheet or layer 9 until they are turned over to web 2; in other words, that web 1 is not divided obliquely when the sections 7, 8 containing active substance are being formed.

The pressure-sensitive layer can be produced, for example, from a polymer matrix with a base polymer and, if necessary, the usual additives. Suitable polymers are, for example, silicons, rubber, synthetic homopolymers, copolymers or block polymers resembling rubber, polyacrylates and their copolymers and esters of hydrogenated colophony. All the polymers used in the production of pressure-sensitive adhesives—and which are biocompatible—are suitable. Especially favoured are those which are block copolymers with a styrene and 1,3-diene basis, polyisobutylenes or polymers and copolymers of acrylate and/or methyl acrylate. Of the block copolymers on a styrene and 1.3-diene basis, linear styrene-isoprene-styrene-block copolymers are preferably employed.

The active substance reservoir layer can be made from a self-adhesive polymer matrix and the active substance, whereby the polymer matrix can be produced from a base material and, if necessary, the usual additives. The choice of base polymer depends on the chemical and physical properties of the active substance. The polymers can be selected from the same group as that of the adhesive layer devoid of active substance.

Substances which are applied to the skin with or without absorbifacients and which produce a local or systemic effect are used as active substances.

Substances producing a local action are, for example, anhydrotics, fungicides, bactericides and bacteriostats.

Substances producing a systemic effect are, for example, antibiotics, hormones, antipyretics, antidiabetics, coronary artery dilators, cardioactive glycosides, spasmolytics, antihypertensives, psychopharmacological drugs, migraine remedies, corticoids, analgesics, contraceptives, antirheumatic agents, anti-cholinergics, symatholytic drugs, sympathomimetics, vasodilators, anticoagulants and antiarrhythmic drugs.

Possible additives, dependent on the polymer and the active substance being used, are softeners, tackifiers, stabilizers, carriers, diffusion and penetration-regulating additives or fillers. The biocompatible substances which are suitable are known. The self-adhesiveness of the reservoir layer must guarantee permanent contact with the skin. As mentioned, the adhesive force of the reservoir layer must be sufficient on its own to ensure the reliable adhesion of the reservoir layer, as this is the pre-requisite for the adequate release of the active substances of the system. It cannot be compensated by means of the pressure-sensitive adhesive edge free of active substance.

The protective layer to be detached prior to application can, for instance, be made of the same materials as those used to produce the backing layer. The latter must, however, be rendered detachable, for example by means of a silicon treatment. Other protective layers which can be removed are, for example, tetrafluoroethylene, treated paper, cellophane, polyvinyl chloride and the like. If it is intended to provide a barrier layer to prevent the diffusion of the active substance or the softener from the active substance reservoir and into the layers free of active substance during the storage of the systems, then this can, for example, be made of the same material as a backing layer which is also to be provided.

The invention will be described in more detail, by means of the following Embodiments.

EXAMPLE 1

In FIG. 1 the web is a 35 mm wide web-shaped laminate, which, seen from the bottom towards the top, is made of a siliconized 100 μm thick PET film, which serves as a carrier sheet; a 80 g/m² strong layer containing active substances, 70% being a solvent polyacrylate as a pressure-sensitive adhesive, 15% a softener and 10% the active substance physostigmine base and a 15 μm thick PET auxiliary sheet. The second web 2 has a width amounting to 56 mm and consists to begin with solely of a 100 μm strong siliconized PET film. The auxiliary sheet and the layer containing active substance are separated with punch 3 vertically to the direction of the web, using a straight cut, resulting in the formation of square sections measuring 35 mm×35 mm. The carrier sheet remains intact. The web-shaped laminate containing active substance is transported from right to left during the movement phase, with the aid of the adjustable clamp 4 of the clamp device and held tight in the stationary or inoperative phase with the aid of hold-down plate 5. The sections 7 containing active substance are detached from the carrier sheet 9 by means of the transfer device, which is formed as a dispenser edge 6. FIG. 1 shows the dispenser edge in its rear dead centre. Section 8 has detached itself from the dispenser edge and has been applied completely to the second web. The webs are still in the stationary or inoperative phase, but the hold-down plate 5 has already opened and the clamp special feature 4 has closed. In FIG. 2 the front dead centre has been reached. The clamp device 4, the dispenser edge 6 and the web 1 have been moved up by one section length.

EXAMPLE 2

Reference is made to FIG. 4.

The first web-shaped laminate i exhibits a 50 mm wide layer lying at the bottom, containing active substance, having a weight per area of 100 g/m², and which contains 30% of a solvent polyacrylate, 30% of a softener, 32% of a polyvinyl resin and 8% of the active substance physostigmine base, and a 100 μm strong PET film lying on the top as a carrier sheet. The coating containing active substance is only moderately adhesive. All the parts of the device which come into contact with it are provided with a coating which is adhesive-repellent. The second web 2 is 72 mm wide and is made of a 15 μm strong PET film with a self-adhesive coating. The layer containing active substance, lying at the bottom, is severed with punch 3, square sections measuring 50 mm×50 mm being formed. The carrier sheet remains intact. The web-shaped laminate containing active substance is transported from right to left with the aid of the movable clamp 4 of the clamp device during the movement phase and held fast with the aid of the hold-down device 5 during the stationary or inoperative phase. Laminating roll 12, which is moved backwards and forwards in synchronism with the clamp device 4, serves as a transfer device. In addition it also performs a movement in the vertical direction, thus free-wheeling during the forward stroke and pressing both the webs onto the laminating table 13 during the reverse stroke. The latter phase is shown in FIG. 4. The section 7 containing active substance is laminated onto the second web 2 by means of the laminating roll 12, following which the carrier sheet 9 of the first web 1 is stripped, using the guide roll 11. As web 2 has been moved on by 72 mm, an intervening space of 22 mm has been formed vis-a-vis the section 7 containing active substance which had been handed over previously.

It can be recognized that the dividing of the layer containing active substance and the transfer of the sections containing active substance take place either simultaneously or immediately after one another. The laminating roll 12 is connected mechanically to the clamp device, so that they perform the same movement.

A smooth operation of the machine can be achieved. The sections containing active substance are applied free of wrinkles, despite the limited thickness of the auxiliary layer. There are no problems whatsoever with adhesive bridges. Up to 6,000 pieces/h can be achieved in a cycle.

We claim:

1. A process for the production of transdermal therapeutic systems, wherein an active substance-containing layer, which is initially present as a layer on a tape or web (1) which tape or web is in the form of a laminate having at least one carrier sheet and optionally having additional auxiliary or protective layers, is transferred in sections, either as a layer on its own or in combination with at least one further auxiliary or protective layer, onto the center of a second, broader web (2), said tape or web (1) and said second web (2) being advanced stepwise with different phases of motion and stationary or inoperative phases, or with different step lengths or at different speeds and the active substance-containing layer and, if present, further auxiliary or protective layers with the exception of the carrier sheet are subdivided, said subdivision being effected during each stationary or inoperative phase of the webs (1,2), in phases and in the same appliance, vertically to the direction of the web, to form active substance-containing sections (7,8) of a size suitable for application to a patient, the process of transferring and subdivision occurring in the same appliance and wherein the transfer of the active substance-containing sections (7,8) onto the second web (2) is effected with concurrent removal of the carrier sheet (9) during a stationary or inoperative phase of the webs (1,2) and utilizing a transfer device which reciprocates in the direction of the web by means of the self-movement of said transfer device, and which is provided with a clamp feed device (4) and a dispenser edge (6).

2. A process according to claim 1, wherein the transfer of the active substance-containing sections (7,8) is effected utilizing a transfer device having a laminating roll (12) and a laminating table (13).

3. A process according to claim 1, wherein the layer containing active substance in the tape or web (1) is positioned as a self-adhesive layer between an auxiliary layer and a sheet with an adhesive-repellent finish, and the sections (7) containing active substance and the auxiliary layer are transferred to the second web (2), formed as an adhesive-repellent sheet, in such a way that the layer containing active substance lies directly on the sheet provided with the adhesive-repellent finish.

4. A process according to claim 2 or 3, wherein the layer containing active substance in the tape or web (1) is positioned as a self-adhesive or non-adhesive layer between an auxiliary layer and the carrier sheet which is adhesive-repellent and the sections containing active substance, formed from the layer containing active substance and the auxiliary layer, are transferred by means of the transfer device to the self-adhesive coated second web in such a way that the auxiliary layer lies directly on the self adhesive sheet.

5. A process according to claim 1 or 2, wherein the layer containing active substance in the tape or web (1) is present as a laminate of three or more layers on a carrier sheet and the sections (7) containing active substance are transferred to the second web (2) in the same order or the reciprocal order of the layers.

6. A process according to claim 1 or 2, wherein the layer containing active substance is applied to the carrier sheet as a non-adhesive coat.

7. A process according to claim 1 or 2, wherein the movement of the transfer device and the movement of a clamp device (4) used for the forward movement of the first web (1) are coupled to one another.

8. A process according to claim 1 or 2, wherein the transfer device, in addition to its movement in the direction of the web, is moved at right angles to-the direction of the web and, during the inoperative or stationary phase of the webs (1, 2), is pressed against the second web (2).

9. A device for carrying out the process according to claim 1, wherein for stripping the delaminated carrier sheet (9) of the first web (1), a first deflection or laminating roll (10 or 12, respectively), which can be moved together with the transfer device, and a second, fixed deflection roll (11) are provided, and wherein the stripped-off carrier sheet (9) on the transfer device is, initially, deflected by an angle of about 135 to 180 degrees and, thereafter, by the movable deflection roll (11) in the opposite direction, on average by about 120 degrees, the angle in the front position of the transfer device not amounting to less than about 100 degrees and in the rear position of the transfer device to not more than about 140 degrees.

* * * * *